US009579303B2

(12) United States Patent
Chen et al.

(10) Patent No.: US 9,579,303 B2
(45) Date of Patent: Feb. 28, 2017

(54) COMPOSITIONS CONTAINING POLYSACCHARIDES

(75) Inventors: Chyi-Cheng Chen, Binningen (CH); Bruno H. Leuenberger, Allschwil (CH)

(73) Assignee: DSM IP ASSETS B.V., Heerlen (NL)

( * ) Notice: Subject to any disclaimer, the term of this patent is extended or adjusted under 35 U.S.C. 154(b) by 1946 days.

(21) Appl. No.: 11/884,433

(22) PCT Filed: Feb. 14, 2006

(86) PCT No.: PCT/EP2006/001331
§ 371 (c)(1),
(2), (4) Date: Aug. 15, 2007

(87) PCT Pub. No.: WO2006/087164
PCT Pub. Date: Aug. 24, 2006

(65) Prior Publication Data
US 2008/0193575 A1    Aug. 14, 2008

(30) Foreign Application Priority Data

Feb. 15, 2005  (EP) ..................................... 05003166

(51) Int. Cl.
*A61K 36/00* (2006.01)
*A61K 31/352* (2006.01)
*A61K 36/48* (2006.01)
*A61K 9/16* (2006.01)

(52) U.S. Cl.
CPC .......... *A61K 31/352* (2013.01); *A61K 9/1652* (2013.01); *A61K 36/48* (2013.01)

(58) Field of Classification Search
None
See application file for complete search history.

(56) References Cited

U.S. PATENT DOCUMENTS

| | | | |
|---|---|---|---|
| 3,499,784 A | | 3/1970 | Organon |
| 5,830,887 A | * | 11/1998 | Kelly |
| 6,143,337 A | | 11/2000 | Fishman et al. |
| 6,413,546 B1 | | 7/2002 | He et al. |
| 6,669,956 B2 | * | 12/2003 | He et al. |
| 6,720,022 B1 | * | 4/2004 | Arnaut et al. |
| 2001/0005514 A1 | | 6/2001 | Chen et al. |
| 2001/0029248 A1 | | 10/2001 | Waggle et al. |
| 2002/0076455 A1 | | 6/2002 | Paul et al. |
| 2003/0059514 A1 | | 3/2003 | Villagran et al. |
| 2004/0033903 A1 | | 2/2004 | Kuellmer et al. |
| 2005/0130912 A1 | * | 6/2005 | Park et al. |

FOREIGN PATENT DOCUMENTS

| | | | |
|---|---|---|---|
| CN | 1485325 A | * | 3/2004 |
| DE | 2128378 A | * | 7/1976 |
| EP | 1110550 A2 | | 6/2001 |
| JP | H1121246 A | | 1/1999 |
| JP | H1149694 A | | 2/1999 |
| JP | H11302201 A | | 11/1999 |
| JP | 2001181185 A | | 7/2001 |
| JP | 2004532829 | | 10/2004 |
| JP | 2005501833 A | | 1/2005 |
| WO | WO 99/03892 A1 | | 1/1999 |
| WO | WO 03/011339 | | 2/2003 |
| WO | WO 03/020265 A2 | | 3/2003 |
| WO | WO 03/049689 | | 6/2003 |
| WO | WO 2004/009576 A2 | | 1/2004 |
| WO | WO 2004/084885 A1 | | 10/2004 |

OTHER PUBLICATIONS

Degenhardt, A et al. Eur Food Res Tech (2001); 213: 277-280. Isolation and purification of isoflavones from soy flour by high-speed countercurrent chromatography.*
Pandjaitan, N. et al., "Enrichment of Genistein in Soy Protein Concentrate with Hydrocolloids and β-Glucosidase," J. Food Sci., vol. 65, No. 4, pp. 591-595 (2000).
Pandjaitan, N. et al., "Enrichment of Genistein in Soy Protein Concentrate with Hydrocolloids and beta-Glucosidase," J. Food Sci., vol. 65, No. 4, pp. 591-595 (2000).
Herbstreith & Fox, "Techniques for the Addition of Pectin Into the Product Batch", (Technical Application Information), pp. 1-4, Mar. 30, 2009, Herbstreith & Fox Corporate Group. (http://www.herbstreith-fox.de/fileadmin/tmpl/pdf/awtinfo/AWT_Techniques_for_the_Addition_of_Pectin.pdf).
Barnes, "The Biochemistry, Chemistry and Physiology of the Isoflavones in Soybeans and their Food Products", Lymphatic Research and Biology, 8(1): 89-97 (2010).
Database CAPLUS on STN Acc. No. 2004:757096, 2004 (Abstract Only).
Dictionary of Dried Foods, Asakura Publishing Co., Ltd., 1984, p. 403-405.

(Continued)

*Primary Examiner* — Qiuwen Mi
(74) *Attorney, Agent, or Firm* — Hoxie & Associates LLC

(57) ABSTRACT

The disclosure relates to compositions, preferably in the form of a powder and/or granules, which contain as principal components a first component selected from the group consisting of isoflavones, soy products containing at least one isoflavone, and mixtures thereof, together with a polysaccharide as second component. A preferred first component is genistein or a pharmaceutically acceptable salt or derivative thereof (e.g. genistin). A preferred second component is pectin. The disclosure further relates to a process for the manufacture of such compositions, and their use in dietary supplements, pharmaceutical and personal care compositions. The disclosure is also directed to the use of a polysaccharide for improving the flowability of a component selected from the group consisting of isoflavones, soy products, preferably those containing at least one isoflavone, and mixtures thereof.

20 Claims, No Drawings

(56) References Cited

OTHER PUBLICATIONS

Mohnen, "Pectin structure and biosynthesis", Current Opinion in Plant Biology, 11:266-277 (2008).
Shangraw, "Direct compression or wet granulation or something in between: that is the question" Indian Journal of Pharmaceutical Sciences, 50(5): 247-252 (1988).
Bibliographic Data and Abstract of Japanese Publication JPH1121246 (A), published Jan. 26, 1999, Espacenet, Date Accessed: Feb. 17, 2016 (Abstract).
Bibliographic Data and Abstract of Japanese Publication JPH1149694 (A), published Feb. 23, 1999, Espacenet, Date Accessed: Feb. 17, 2016 (Abstract).
Bibliographic Data and Abstract of Japanese Publication JPH11302201 (A), published Nov. 2, 1999, Espacenet, Date Accessed: Feb. 17, 2016 (Abstract).
Bibliographic Data and Abstract of Japanese Publication JP2001181185 (A), published Jul. 3, 2001, Espacenet, Date Accessed: Feb. 17, 2016 (Abstract).
Bibliographic Data and Abstract of Japanese Publication JP2004532829 (A), published Oct. 28, 2004, Espacenet, Date Accessed: Feb. 17, 2016 (Abstract).
Bibliographic Data and Abstract of Japanese Publication JP2005501833 (A), published Jan. 20, 2005, Espacenet, Date Accessed: Feb. 17, 2016 (Abstract).
Pharmacy I, Prescription and Formulation, Asakura Publishing Co., Ltd., 1995, pp. 59-62, 4 pages (Japanese Language Translation).
Takayama Akira, Supplement, Chemical Industry, 1983, vol. 27, No. 17, pp. 197-202, 6 pages (Japanese Language Translation).

\* cited by examiner

COMPOSITIONS CONTAINING POLYSACCHARIDES

CROSS REFERENCE TO RELATED APPLICATIONS

This application is the National Stage of International Application No. PCT/EP2006/001331, filed Feb. 14, 2006, which claims benefit of European Patent Application No. 05003166.5, filed Feb. 15, 2005, the contents of each of which are incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

BACKGROUND OF THE INVENTION

Field of the Invention

The present invention relates to compositions comprising as principal components a first component selected from the group consisting of isoflavones, soy products containing at least one isoflavone, and mixtures thereof, and a polysaccharide as second component. A preferred first component is genistein, a preferred second component is pectin.

The present invention further relates to a process for the manufacture of such compositions, and their use in dietary supplements, pharmaceutical and personal care compositions.

The present invention is also directed to the use of a polysaccharide for improving the flowability of a component selected from the group consisting of isoflavones, soy products, preferably those containing at least one isoflavone, and mixtures thereof.

Description of Related Art Including Information Disclosed Under 37 CFR 1.97 and 1.98

Genistein is a bioactive isoflavone naturally found e.g. in soy and commercially available. It has been claimed to be useful as an anti-inflammatory agent, for prevention and treatment of osteoporosis and heart disease, for prevention of photodamage and aging skin and wrinkles, for inhibition of Alzheimer's disease and for treatment of menopausal symptoms, estrogen disorders, cancer, cataracts, cystic fibrosis and migraine. Amongst the voluminous literature in this field, M. Messina, Chemistry & Industry 1995, 413-415, and T. E. Wiese et al., ibid. 1997, 648-653, present interesting reviews on the biological effects and uses of isoflavones, including genistein.

BRIEF SUMMARY OF THE INVENTION

BRIEF DESCRIPTION OF THE SEVERAL DRAWINGS

Not Applicable

Genistein is normally produced in crystalline powder form e.g. according to a process as disclosed in WO 2004/009576. Such a powder form has a very poor flowability. The poor powder flowability renders the crystalline powder difficult for use in making tablets and other application forms that require the powder to be free flowing. The same problem occurs if one tries to make tablets of other isoflavones or soy products, preferably of those containing at least one isoflavone, more preferably of those soy products containing at least one isoflavone and being essentially free of soy proteins and/or of phytosterols.

Compositions which have solved this problem known in the prior art are compositions of polysaccharides with compounds such as (−)-epigallocatechin gallate (WO 03/011339) and L-ascorbic acid (EP-A 1 110 550, WO 03/020265, US 2001/0005514), where the flowability of the compounds was improved by the addition of a polysaccharide. The compounds (−)-epigallocatechin gallate and L-ascorbic acid are, however, water-soluble, whereas the isoflavones such as genistein are generally hardly or essentially not water-soluble. Furthermore, (−)-epigallocatechin gallate and L-ascorbic acid are structurally different to the present compounds.

It was, thus, not to be expected to find out that a composition containing isoflavones and/or soy products containing at least one isoflavone, most preferably a composition containing (a soy product containing at least the isoflavone) genistein and/or its glucoside genistin, and a polysaccharide, preferably in the form of a powder or of granules, has also improved flowability. That means that the polysaccharide acts here as granulating agent.

Thus, in one aspect, the present invention relates to a composition comprising:
(a) a first component selected from the group consisting of isoflavones, soy products containing at least one isoflavone, and mixtures thereof, and
(b) a second component which is a polysaccharide.

Preferably the composition is in the form of a powder or granules. In each granule or powder particle, an individual isoflavone crystal (especially an individual genistein crystal) or several crystals is/are coated or partially coated with the polysaccharide. The coated or partially coated crystal or crystals are held (glued) together by the polysaccharide, which functions as a binder, to form a granule with appropriate size.

DETAILED DESCRIPTION OF THE INVENTION

The composition according to the present invention has preferably a water activity of from 0.05 to 0.7, preferably of from 0.1 to 0.5, more preferably of from 0.2 to 0.5. The water activity is measured using a Novasina Thermoconstanter TH200 (Novasina AG, Zürich, Switzerland).

First Component a)

In a preferred embodiment of the present invention the isoflavone is of the general formula I,

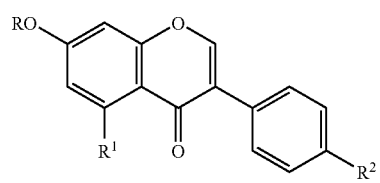

I wherein R signifies hydrogen (phenols), $C_{1-18}$-alkyl (ether) or $C_{1-18}$-alkylcarbonyl (ester), $R^1$ signifies hydrogen or hydroxyl or $C_{1-18}$-alkyloxy or $C_{1-18}$-alkylcarbonyloxy, and $R^2$ signifies hydroxyl or $C_{1-18}$-alkoxy or $C_{1-18}$-alkylcarbonyloxy. Preferred isoflavones of the general formula I are 7-hydroxy- or 5,7-dihydroxy-2H-isoflavones wherein R is hydrogen and $R^1$ signifies hydrogen or hydroxyl, and $R^2$ signifies hydroxyl or $C_{1-6}$-alkoxy such as methoxy and ethoxy, as well as derivatives and pharmaceutically acceptable salts thereof. A process for their manufacture is e.g. described in WO 2004/009576.

The term "alkyl" encompasses straight-chain, as well as branched-chain alkyl. The term "alkyloxy" encompasses straight-chain, as well as branched-chain alkyloxy.

Most preferably the first component is selected from the group consisting of genistein (compound of the formula I with R being hydrogen and $R^1$ and $R^2$ both being hydroxyl), pharmaceutically acceptable salts and/or pharmaceutically acceptable derivatives thereof. Most preferably the first component is genistein. The isoflavones, e.g. genistein, can be isolated from natural sources and optionally highly purified or chemically synthesized. In a most preferred embodiment the isoflavones of the present invention, e.g. genistein, to be compounded according to the present invention are in crystalline form.

Preferably the used genistein (or pharmaceutically acceptable salt or pharmaceutically acceptable derivative thereof) has a particle size in the range of from 10 μm to 1000 μm, more preferably in the range of from 30 μm to 500 μm, even more preferably in the range of from 30 μm to 200 μm, most preferably in the range of from 50 μm to 200 μm.

Examples of pharmaceutically acceptable derivatives are glycosides, especially the β-glucoside conjugates such as the glucosides preferred example: genistin), the malonylglucosides and the acetylglucosides.

Examples of pharmaceutically acceptable salts are compounds of the formula I, wherein R is $Na^+$, $K^+$, ½ $Ca^{2+}$ or ½ $Mg^{2+}$ and/or $R^1$ and/or $R^2$ are independently from each other $ONa^+$, $OK^+$, $O(½ Ca^{2+})$ or $O(½ Mg^{2+})$.

In another embodiment of the present invention the first component a) is selected from the group consisting of isoflavones, soy products containing at least one isoflavone, and mixtures thereof, wherein at least one isoflavone has a solubility of below 5% in water at 30° C. and/or wherein at least one isoflavone has a solubility of below 5% in methylene chloride at 30° C.

In a further embodiment of the present invention the first component a) is selected from the group consisting of isoflavones, soy products containing at least one isoflavone, and mixtures thereof, wherein at least one isoflavone has a solubility in the range of from 0.001 to 5% in water at 30° C. and/or wherein at least one isoflavone has a solubility in the range of from 0.001 to 5% in methylene chloride at 30° C.

"%" in the context of the present invention, especially in the context of the solubilities, means "weight-%" if not stated otherwise. The solubilities if not stated otherwise are determined at an absolute pressure of 1 bar.

Preferably all isoflavones present in a composition according to this embodiment of the present invention have a solubility of below 5% in water at 30° C. and/or a solubility of below 5% in methylene chloride at 30° C. In a further embodiment of the present invention all isoflavones present in a composition according to the present invention have a solubility in the range of from 0.001 to 5% in water at 30° C. and/or a solubility in the range of from 0.001 to 5% in methylene chloride at 30° C.

More preferably all isoflavones present in a composition according to this embodiment of the present invention have a solubility of below 5% in water at 30° C. and a solubility of below 5% in methylene chloride at 30° C. In a further embodiment of the present invention all isoflavones present in a composition according to the present invention have a solubility in the range of from 0.001 to 5% in water at 30° C. and a solubility in the range of from 0.001 to 5% in methylene chloride at 30° C.

The term "soy product" encompasses extracts as well as concentrates obtained from soy including any chemically (especially enzymatically), thermally, physically and/or by UV radiation treated material. Preferred is such soy product that contains at least one isoflavone (especially of the formula I with the definitions and preferences as cited above, most preferred genistein (and its pharmaceutically acceptable salts and derivatives)) in an amount of at least 50 weight-%, preferably in an amount of at least 70 weight-%, more preferably in an amount of at least 80 weight-%, most preferably in an amount of at least 90 weight-%, based on the total weight of the soy product.

In another preferred embodiment of the composition of the present invention the soy product containing at least one isoflavone is essentially free of soy proteins or of phytosterols.

In a further preferred embodiment of the composition of the present invention the soy product containing at least one isoflavone is essentially free of soy proteins and of phytosterols.

The term "phytosterol" in the context of the present invention encompasses especially plant sterols selected from the group consisting of β-sitosterol, campesterol, stigmasterol, sitostanol and campestanol.

"Essentially free" in the context of the present invention means that the amount of soy protein and/or of phytosterols in the soy product (or in other forms, compositions and products of the present invention as mentioned below) is ≤7% by weight, preferably ≤5% by weight, more preferably ≤3% by weight, even more preferably ≤2% by weight, most preferably ≤1% by weight, based on the total weight of the soy product (and of other forms, compositions and products of the present invention as mentioned below, respectively), preferably it means that only traces of soy protein and/or of phytosterols are present.

In another preferred embodiment of the present invention the composition itself is essentially free of soy protein and/or phytosterol, preferably it is essentially free of both of them.

The preferred particle size distribution of the composition of the present invention, preferably in form of a powder or of granules, is as follows:

at least 95% of the particles have a size of ≤1500 μm (preferred: ≤1000 μm, more preferred ≤850 μm), whereby at most 35% of the particles have a size of ≤50 μm (preferred: ≤100 μm, more preferred ≤150 μm).

In another preferred embodiment of the present invention particle size distribution of the composition of the present invention, preferably in form of a powder or of granules, is as follows:

at least 95% of the particles have a size in the range of from 10 μm to 1500 μm (preferred: in the range of from 10 μm to 1000 μm, more preferred in the range of from 10 μm to 850 μm), whereby at most 35% of the particles have a size in the range of from 10 μm to 50 μm (preferred: in the range of from 10 μm to 100 μm, more preferred in the range of from 10 μm to 150 μm).

Second Component b): Polysaccharides

The term "polysaccharides" is used in the conventional way as understood by the person skilled in the art.

Examples of polysaccharides for use in the present invention (as granulating agent) are pectin, alginates, starch, cellulose derivatives such as hydroxypropyl methyl cellulose and carboxymethyl cellulose, carrageenan, agar, gum arabic, guar gum, xanthan gum and mixtures thereof. Preferred examples of polysaccharides for use in the present invention are pectin, alginates, starch, carrageenan, agar, gum arabic, guar gum, xanthan gum and mixtures thereof. The even more preferred polysaccharide is pectin or alginate or a mixture thereof, most preferred is pectin.

Pectin is a polysaccharide and described for example in the book entitled Industrial Gums, third edition, Academic Press, Inc., 1993, pages 257ff. as well as in EP-A 1 110 550. Pectins used in the present invention are generally commercially available and e.g. produced from citrus peel or apple (pomace). Other possible sources are sugarbeet, sunflower and mango. Preferred pectins to be used within the scope of the present invention are citrus pectins, which generally have lighter colour than apple pectins and, thus, do not contribute significant colour to the final product.

In an embodiment of the invention high molecular weight pectin may be used. The term "high molecular weight pectin" as used herein denotes pectin having a molecular weight of more than about 300 kDalton. The preferred high molecular weight pectins are those having a molecular weight of from about 300 kDalton to about 400 kDalton, particularly 350 kDalton. Such pectins can be obtained as disclosed in U.S. Pat. No. 6,143,337 the contents of which are incorporated herein by reference. The molecular weight is determined by size exclusion chromatography having a multi angle laser light scattering detector as described in U.S. Pat. No. 6,143,337. However, pectins of higher molecular weight, e.g. up to 2.000 kdalton can be used also in the present invention. Pectins of such molecular weight can be obtained e.g. from Asteraceae plants, especially cichory and Jerusalem artichoke, see WO 99/03892. Fractions of the desired high molecular weight can be obtained from such pectins by membrane filtration, e.g. using polyethersulfone or composite regenerate cellulose membranes as supplied by Millipore Corporation, Bedford, Mass. 01730, USA, under the trade name Pellicon® Tangential Flow Filtration Cassettes.

The polysaccharide is preferably used in quantities≥0.1% by weight, more preferably in quantities≥0.5% by weight. Also preferred is the use of the polysaccharide in quantities≤15% by weight, more preferably in quantities≤5% by weight, most preferably in quantities≤3% by weight, based on the sum of the weight of the polysaccharide and the component a). In a further preferred embodiment of the composition of the present invention the polysaccharide is used within the range of from 0.1% to 15% by weight, more preferably in quantities within the range of from 0.1% to 5% by weight, most preferably in quantities within the range of from 0.5% to 3% by weight, based on the total weight of the composition, especially based on the sum of the weight of the polysaccharide and the component a).

If pectin is used as the polysaccharide, it is preferably used in quantities≥0.1% by weight, more preferably in quantities≥0.5% by weight, most preferably in quantities≥1.5% by weight. Also preferred is the use of pectin in quantities≤5% by weight, more preferably in quantities≤2.5% by weight, most preferably in quantities≤2% by weight, based on the sum of the weight of the pectin and the component a). In a further preferred embodiment of the composition of the present invention the pectin is used in quantities of from 0.1% to 5% by weight, more preferably in quantities within the range of from 1.5% to 2.5% by weight, most preferably within the range of from 0.5% to 2% by weight, based on the total weight of the composition, especially based on the sum of the weight of the pectin and the component a).

If alginate is used as the polysaccharide, it is preferably used in quantities≥0.1% by weight, more preferably in quantities≥0.5% by weight. Also preferred is the use of alginate in quantities≤5% by weight, more preferably in quantities≤2% by weight, based on the sum of the weight of the alginate and the component a). In a further preferred embodiment of the composition of the present invention the alginate is used in quantities of from 0.1% to 5% by weight, more preferably in quantities within the range of from 0.5% to 2% by weight, based on the total weight of the composition, especially based on the sum of the weight of the alginate and the component a).

If starch is used as the polysaccharide, it is preferably used in quantities≥0.1% by weight, more preferably in quantities≥0.5% by weight. Also preferred is the use of starch in quantities≤15% by weight, more preferably in quantities≤5% by weight, most preferably in quantities≤2% by weight, based on the sum of the weight of the starch and the component a). In a further preferred embodiment of the composition of the present invention the starch is used in quantities of from 0.1% to 15% by weight, more preferably in quantities within the range of from 0.1% to 5% by weight, most preferably in quantities within the range of from 0.5% to 2% by weight, based on the total weight of the composition, especially based on the sum of the weight of the starch and the component a).

In a further aspect, the present invention relates to a process for the manufacture of the composition of the present invention.

Manufacture of the Composition

The composition of this invention may be produced by any method known per se for the production of powders or granules. Preferred are fluidized-bed granulation, high-shear granulation, extrusion, spray-drying and wet granulation. The present invention is also directed to the manufacture of the composition of the present invention by those processes.

For obtaining the composition of the present invention by spray-drying it is convenient to prepare an aqueous slurry of all the components or a slurry of all components in a solvent or solvent mixture which is able to dissolve the polysaccharide, preferably the pectin. A preferred example of such a solvent is water. The slurry has preferably a solid content of 10 to 70% by weight, and preferably of 25 to 50% by weight, based on the total weight of the slurry. The slurry is then spray-dried in a manner known per se.

Thus another aspect of the present invention is a process for the manufacture of a composition as mentioned above, which comprises preparing a slurry, preferably an aqueous slurry, of all the components, preferably having a solid content of 10 to 70% by weight, and preferably 25 to 50% by weight, based on the total weight of the slurry, and spray-drying the slurry in a manner known per se.

For obtaining the composition of the present invention by fluidized-bed granulation it is convenient to use a known fluidized-bed granulating apparatus which comprises a fluidized-bed drying device fitted with spray means. Preferably the first component forms the fluidized bed, the fluidized bed being fluidized by air or an inert gas, e.g. nitrogen. The polysaccharide or polysaccharides are dissolved in an appropriate amount of water or solvent (mixture) capable of dissolving the polysaccharide(s), preferably in an appropriate amount of water, and sprayed in the form of an atomized mist onto the fluidized particles in such a manner that the granulating and drying operations is accomplished in a single step. This proceeding is the best mode of the invention.

Alternatively, the polysaccharide or polysaccharides are mixed with the first component and the fluidized bed being fluidized by air or an inert gas, e.g. nitrogen. An appropriate amount of water or solvent (mixture) capable of dissolving the polysaccharide(s), preferably an appropriate amount of water, is sprayed in the form of an atomized mist onto the fluidized particles in such a manner that the granulating and drying operations is accomplished in a single step. The granulating process is continued until the desired granule or powder is obtained.

At the end of the granulation process, the granules may be sieved to fractionate the granules as to size. While the particle size is not narrowly critical to the invention it is, for practical purposes, preferably within 50 and 1500 µm, more preferably between 100 and 1000 µm, most preferably from 150 to 850 µm.

Therefore, a further aspect of the present invention is a process for the manufacture of a composition as mentioned above, which comprises forming a fluidized bed of the first component with or without polysaccharide within a fluidized-bed drying device fitted with spray means, said fluidized bed being fluidized by air or an inert gas, and spraying a solution, preferably an aqueous solution, of a polysaccharide or only water or the solvent (mixture) in the form of an atomized mist onto the fluidized particles until the desired granule or powder is obtained.

Preferably one of the components/the first component of the processes mentioned above is an isoflavone of the formula I with the definitions and preferences as disclosed above or a pharmaceutically acceptable salt or derivative thereof. A preferred polysaccharide used in the processes as mentioned above is pectin, alginate or a mixture thereof, more preferred is pectin.

The composition thus obtained may be further processed depending on the intended use of the first component or desired applications. For instance, the composition may be compressed into tablets with conventional tabletting methods and machinery.

Optionally the compositions, preferably the powder or the granules, may further be mixed with a lubricant or a mixture of lubricants and then compressed into tablets. If additional lubricant is used it is preferably selected from the group of stearic acid or the magnesium or calcium salt thereof, or glyceryl behenate 45 (Compritol 888 ATO), preferably in an amount of 0.5 to 4% by weight, based on the total weight of the composition.

Alternatively or additionally the composition may be mixed with excipients. Examples of excipients are (microcrystalline or powdered) cellulose, (pregelatinized) starch, lactose (anhydrous or monohydrate), sorbitol, mannitol, calcium carbonate, dibasic calcium phosphate (dehydrate), tribasic calcium phosphate, calcium sulphate, dextrates, dextrin, dextrose, fructose, kaolin, lactitol and (dextrinized) sucrose. Dextrinized sucrose is e.g. commercially available under the trade name Di Pac® sugar from Tate and Lyle North American Sugars, Inc., Canada, or from Domino Specialty Ingredients, Baltimore, Md. USA.

The composition of the present invention may also be mixed with adjuvants.

Furthermore the present invention is directed to dosage forms based on a composition of the present invention comprising the first and second component as defined above, most preferably comprising a) genistein (or pharmaceutically acceptable salts or derivatives thereof) and b) pectin, such as tablets, pills, granules, dragées, capsules, and effervescent formulations such as powders and tablets. Preferably the dosage form is a tablet.

In a preferred embodiment of dosage forms of the present invention these dosage forms themselves are essentially free of soy protein and/or of phytosterols, preferably they are essentially free of both of them.

A further object of the present invention are dietary as well as pharmaceutical and personal care compositions comprising
  a) a first component selected from the group consisting of isoflavones, soy products containing at least one isoflavone, and mixtures thereof, and
  b) a second component which is a polysaccharide.

For the dietary, pharmaceutical and personal care compositions the same preferences for the first and second component as mentioned above apply.

Furthermore, in a preferred embodiment of the dietary, pharmaceutical and personal care compositions of the present invention these dietary, pharmaceutical and personal care compositions themselves are essentially free of soy protein and/or of phytosterols, preferably they are essentially free of both of them.

The term "dietary compositions" comprises any type of (fortified) food/feed and beverages including also clinical nutrition, and also dietary supplements.

Beverages wherein the composition of the present invention can be used as an ingredient can be carbonated beverages e.g., flavoured seltzer waters, soft drinks or mineral drinks, as well as non-carbonated beverages e.g. flavoured waters, fruit juices, fruit punches and concentrated forms of these beverages. They may be based on natural fruit or vegetable juices or on artificial flavours. Also included are alcoholic beverages and instant beverage powders. Besides, sugar containing beverages diet beverages with non-caloric and artificial sweeteners are also included.

Further, dairy products, obtained from natural sources or synthetic, are within the scope of the food products wherein the composition of the present invention can be used as an ingredient. Typical examples of such products are milk drinks, ice cream, cheese, yoghurt and the like. Milk replacing products such as soymilk drinks and tofu products are also comprised within this range of application.

Also included are sweets which contain the composition of the present invention as an ingredient, such as confectionery products, candies, gums, desserts, e.g. ice cream, jellies, puddings, instant pudding powders and the like.

Also included are cereals, snacks, cookies, pasta, soups and sauces, mayonnaise, salad dressings and the like which contain the composition of the present invention as an ingredient. Furthermore, fruit preparations used for dairy and cereals are also included.

Pharmaceutical compositions such as tablets such as chewable tablets, effervescent tablets or film-coated tablets or capsules such as hard shell capsules wherein the compositions are used as an ingredient are also within the scope of the present invention. The product forms are typically added as powders to the tabletting mixture or filled into the capsules in a manner per se known for the production of capsules.

Animal feed products such as premixes of nutritional ingredients, compound feeds, milk substitutes, liquid diets or feed preparations wherein the compositions are used as an ingredient are also within the scope of the present invention.

Examples of personal care compositions are cosmetics, toiletries and derma products. Therefore, skin and hair care products such as creams, lotions, baths, lipsticks, shampoos, conditioners, sprays or gels wherein the compositions are used as an ingredient are also within the scope of the present invention.

In still another aspect, the invention is concerned with the use of polysaccharides (with the definitions and preferences as disclosed above), particularly with the use of pectin, as mentioned above for improving the flowability of a powder of a component selected from the group consisting of isoflavones, soy products, preferably those containing at least one isoflavone, and mixtures thereof. Or in other words the present invention is also directed to the use of polysaccharides, especially of pectin, as granulating agent for compositions containing a component selected from the group consisting of isoflavones, soy products, preferably those containing at least one isoflavone, and mixtures thereof. For the solubility of the isoflavone(s) the same preferences apply as mentioned above.

Preferably the soy products are essentially free of soy protein and/or of phytosterols (as defined above), preferably they are essentially free of both of them. In another preferred embodiment of the present invention the powder itself is essentially free of soy protein and/or of phytosterols, preferably it is essentially free of both of them.

In another preferred embodiment of the use according to the present invention the soy product contains at least one isoflavone in an amount of at least 50 weight-%, preferably in an amount of at least 70 weight-%, more preferably in an amount of at least 80 weight-%, most preferably in an amount of at least 90 weight-%, based on the total weight of the soy product.

In a preferred embodiment of the invention a polysaccharide, preferably a pectin, is used to improve the flowability of a powder of an isoflavone or of a soy product containing such an isoflavone, especially of a powder of an isoflavone, preferably of an isoflavone of the formula I or of a soy product containing such an isoflavone, more preferably of a powder of such an isoflavone of the formula I,

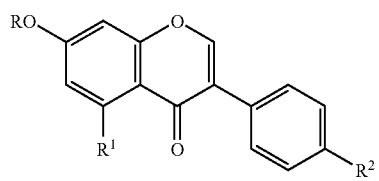

wherein R, $R^1$ and $R^2$ have the same meanings and preferences as mentioned above, or to improve the flowability of a powder of (a soy product containing) a pharmaceutically acceptable salt or a pharmaceutically acceptable derivative of said isoflavone.

In the most preferred embodiment of the present invention a polysaccharide, preferably a pectin, is used to improve the flowability of a powder of an isoflavone of the formula I with $R^1$ and $R^2$ being both hydroxyl (=genistein), of a pharmaceutically acceptable salt or of a pharmaceutically acceptable derivative thereof, preferably of genistein itself.

The invention is illustrated further by the following Examples.

Example 1

A pectin solution was prepared by dissolving 2.47 g of pectin (GENU® pectin USP/100, 8.88% moisture content, CP Kelco, Lille Skensved, Denmark) in 222.5 g of water to give a pectin solution containing 1.0 weight-% pectin, based on the total weight of the pectin solution. Genistein powder was placed in a Glatt Fluidized-Bed granulator (Model Uniglatt, Glatt GmbH, Binzen, Germany) and sprayed with a fine mist of the pectin solution. The granulation conditions were suitably as follows:

| Genistein powder: | 298.5 g |
|---|---|
| Pectin solution: | 150 g |
| Pectin solution spraying rate: | 12 g/minute |

After the completion of spraying the pectin solution, the granules were further dried in the granulator for about 10 minutes. The granules had a water activity of 0.28 and a granule size distribution as shown in Example 5.

Example 2

A pectin solution was prepared by dissolving 3.95 g of pectin (GENU® pectin USP/100, 8.88% moisture content, CP Kelco, Lille Skensved, Denmark) in 176.1 g of water to give a pectin solution containing 2.0 weight-% pectin, based on the total weight of the pectin solution. Genistein powder was placed in a Glatt Fluidized-Bed granulator ((Model Uniglatt, Glatt GmbH, Binzen, Germany) and sprayed with a fine mist of the pectin solution. The granulation conditions were suitably as follows:

| Genistein powder: | 297 g |
|---|---|
| Pectin solution: | 150 g |
| Pectin solution spraying rate: | 15.8 g/minute |

After the completion of spraying pectin solution, the granules was further dried in the granulator for about 10 minutes. The granules had a water activity of 0.17 and a granule size distribution as shown in Example 5.

Example 3

A pectin solution was prepared by dissolving 5.93 g of pectin (GENU® pectin USP/100, 8.88% moisture content, CP Kelco, Lille Skensved, Denmark) in 174.1 g of water to give a pectin solution containing 3.0 weight-% pectin, based on the total weight of the pectin solution. Genistein powder was placed in a Glatt Fluidized-Bed granulator (Model Uniglatt, Glatt GmbH, Binzen, Germany) and sprayed with a fine mist of the pectin solution. The granulation conditions were suitably as follows:

| Genistein powder: | 295.5 g |
|---|---|
| Pectin solution: | 150 g |
| Pectin solution spraying rate: | 14.6 g/minute |

After the completion of spraying pectin solution, the granules was further dried in the granulator for about 10 minutes. The granules had a water activity of 0.25 and a granule size distribution as shown in Example 5.

Example 4

A pectin solution was prepared by dissolving 9.87 g of pectin (GENU® pectin USP/100, 8.88% moisture content, CP Kelco, Lille Skensved, Denmark) in 215.1 g of water to give a pectin solution containing 4.0 weight-% pectin, based on the total weight of the pectin solution. Genistein powder was placed in a Glatt Fluidized-Bed granulator (Model Uniglatt, Glatt GmbH, Binzen, Germany) and sprayed with a fine mist of the pectin solution. The granulation conditions were suitably as follows:

| Genistein powder: | 294 g |
| Pectin solution: | 150 g |
| Pectin solution spraying rate: | 11.8 g/minute |

After the completion of spraying pectin solution, the granules was further dried in the granulator for about 10 minutes. The granules had a water activity of 0.25 and a granule size distribution as shown in Example 5.

Example 5

The granule size distributions of Example 1-4 were analyzed by sieve analysis and the results are shown in the following table. The flowability was determined by the time needed to have 100 g of genistein crystals or genistein granules flowing through an 11-mm orifice of a funnel.

| | % Pectin | Granule Particle Size Distribution [%] | | | | | | | Flowability [seconds/ 100 g] |
| --- | --- | --- | --- | --- | --- | --- | --- | --- | --- |
| | | >850 μm | >800 μm | >600 μm | >425 μm | >250 μm | >150 μm | <150 μm | |
| Genistein crystal | 0 | 0.1 | 0 | 0 | 14.5 | 50 | 28.2 | 7.2 | No flow |
| Example 1 | 0.5 | 0.5 | 0.2 | 3.3 | 7.5 | 20.5 | 28.8 | 39.2 | 16 |
| Example 2 | 1.0 | 1.3 | 0.3 | 3.4 | 8.3 | 40.5 | 32.0 | 14.2 | 13 |
| Example 3 | 1.5 | 3.2 | 0.6 | 6.9 | 12.6 | 46.6 | 22.8 | 7.4 | 12 |
| Example 4 | 2.0 | 11.5 | 2.0 | 16.6 | 19.4 | 26.3 | 13.4 | 10.8 | 9 |

The invention claimed is:

1. A method of improving the flowability of a powder consisting of isoflavone; said method consisting of introducing water-soluble pectin into the powder.

2. The method according to claim 1 wherein the isoflavone is an isoflavone of formula I, a pharmaceutically acceptable salt or a glycoside thereof, wherein formula I is:

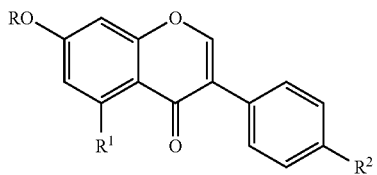

wherein R signifies hydrogen, $C_{1-18}$-alkyl or $C_{1-18}$ alkylcarbonyl, $R^1$ signifies hydrogen or hydroxyl or $C_{1-18}$-alkyloxy or $C_{1-18}$-alkylcarbonyloxy, and $R^2$ signifies hydroxyl or $C_{1-18}$-alkoxy or $C_{1-18}$-alkylcarbonyloxy.

3. The method according to claim 2, wherein R is hydrogen and $R^1$ and $R^2$ are both hydroxyl.

4. The method of claim 1, wherein the water-soluble pectin is introduced in the form of a slurry.

5. The method of claim 4, wherein the slurry is an aqueous slurry.

6. A composition consisting of a powder or a plurality of granules, said powder or plurality of granules consisting of:
a) a first component which is isoflavone in a quantity of 95-99.9 weight %; and
b) a second component which is pectin in a quantity of 0.1-5 weight-%.

7. The composition of claim 6, wherein the isoflavone in the powder, or in the plurality of granules, is coated or partially coated with the pectin.

8. The composition according to claim 6, wherein the isoflavone is selected from the group consisting of isoflavones of formula I, pharmaceutically acceptable salts or glycosides thereof wherein formula I is:

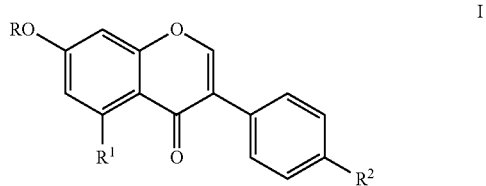

wherein R signifies hydrogen, $C_{1-18}$-alkyl or $C_{1-18}$ alkylcarbonyl, $R^1$ signifies hydrogen or hydroxyl or $C_{1-18}$-alkyloxy or $C_{1-18}$-alkylcarbonyloxy, and $R^2$ signifies hydroxyl or $C_{1-18}$-alkoxy or $C_{1-18}$-alkylcarbonyloxy.

9. The composition of claim 8, wherein the isoflavone in the powder, or in the plurality of granules, is coated or partially coated with the pectin.

10. The composition according to claim 8, wherein R is hydrogen and $R^1$ and $R^2$ are both hydroxyl.

11. The composition of claim 10, wherein the isoflavone in the powder, or in the plurality of granules, is coated or partially coated with the pectin.

12. The composition of claim 6 in a dosage form selected from the group consisting of a tablet, and capsule.

13. The dosage form according to claim 12, wherein the dosage form is a tablet.

14. A dietary, pharmaceutical and personal care composition comprising a composition as claimed in claim 6.

15. A process for the manufacture of a composition according to claim 6, which comprises preparing a slurry of the-components having a solid content of 10 to 70% by weight, based on the total weight of the slurry, and spray-drying the slurry.

16. The process of claim 15, wherein the slurry has a solid content of 25 to 50% by weight.

17. A process for the manufacture of a composition according to claim 6, which comprises forming a fluidized bed of the first component with or without pectin within a fluidized-bed drying device fitted with spray means, said fluidized bed being fluidized by air or an inert gas, and spraying a solution, of a pectin or only water in the form of an atomized mist onto the fluidized particles until the composition is obtained.

18. The process according to claim 15 or 17, wherein the first component is an isoflavone of the formula I,

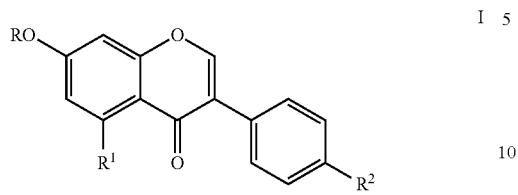

wherein R signifies hydrogen, $C_{1-18}$-alkyl or $C_{1-18}$ alkylcarbonyl, $R^1$ signifies hydrogen or hydroxyl or $C_{1-18}$-alkyloxy or $C_{1-18}$-alkylcarbonyloxy, and $R^2$ signifies hydroxyl or $C_{1-18}$-alkoxy or $C_{1-18}$-alkylcarbonyloxy, or a pharmaceutically acceptable salt or glycoside thereof.

19. The process according to claim 18, wherein R is hydrogen and $R^1$ and $R^2$ are both hydroxyl.

20. A process for the manufacture of a composition according to claim 6, which comprises forming a fluidized bed of the first component within a fluidized-bed drying device fitted with spray means, said fluidized bed being fluidized by air or an inert gas, and spraying an aqueous solution of a pectin and water in the form of an atomized mist onto the fluidized particles until the composition is obtained.

\* \* \* \* \*